(12) United States Patent
Walzade et al.

(10) Patent No.: US 9,040,089 B2
(45) Date of Patent: May 26, 2015

(54) ORAL COMPOSITIONS OF CLINDAMYCIN

(75) Inventors: Kalpana Walzade, Pune (IN); Rajesh Kulkarni, Pune (IN); Shirishkumar Kulkarni, Pune (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 137 days.

(21) Appl. No.: 13/055,004

(22) PCT Filed: Sep. 10, 2008

(86) PCT No.: PCT/IN2008/000579
§ 371 (c)(1),
(2), (4) Date: Jan. 20, 2011

(87) PCT Pub. No.: WO2010/010568
PCT Pub. Date: Jan. 28, 2010

(65) Prior Publication Data
US 2011/0123631 A1    May 26, 2011

(30) Foreign Application Priority Data

Jul. 22, 2008 (IN) .......................... 1242/KOL/2008

(51) Int. Cl.
| | | |
|---|---|---|
| *A61P 33/02* | (2006.01) | |
| *A61P 33/06* | (2006.01) | |
| *A61K 9/00* | (2006.01) | |
| *A61K 9/16* | (2006.01) | |
| *A61K 9/50* | (2006.01) | |

(52) U.S. Cl.
CPC ............. *A61K 9/0095* (2013.01); *A61K 9/1623* (2013.01); *A61K 9/1641* (2013.01); *A61K 9/5026* (2013.01)

(58) Field of Classification Search
None
See application file for complete search history.

(56) References Cited

U.S. PATENT DOCUMENTS

| | | | |
|---|---|---|---|
| 3,580,904 A | | 5/1971 | Morozowich et al. |
| 3,655,885 A | | 4/1972 | Morozowich et al. |
| 5,730,997 A | | 3/1998 | Lienhop et al. |
| 6,806,256 B2 | | 10/2004 | Ulrich et al. |
| 2005/0101936 A1 | * | 5/2005 | Gonzales et al. ............. 604/514 |
| 2005/0192236 A1 | * | 9/2005 | Chao et al. .................. 514/42 |
| 2008/0008765 A1 | | 1/2008 | Schwarz et al. |
| 2009/0155363 A1 | * | 6/2009 | Maibach ....................... 424/484 |

FOREIGN PATENT DOCUMENTS

| | | | |
|---|---|---|---|
| CN | 1977856 A | | 6/2007 |
| EP | 0 429 224 A1 | | 11/1989 |
| EP | 1 671 623 A1 | | 10/2004 |
| WO | WO 03034991 | * | 5/2003 |
| WO | WO 2007/021167 A1 | | 2/2007 |
| WO | WO 2008/030469 A2 | | 3/2008 |

OTHER PUBLICATIONS

Sohi et al. "Taste Masking Technologies in Oral Pharmaceuticals:Recent Developments and Approaches". Drug Development and Industrial Pharmacy vol. 30, No. 5, pp. 429-448, 2004.*
Cleocin Pediatric https://www.pfizer.com/files/products/uspi_cleocin_pediatric.pdf.*
Zhang, W., "Method for manufacturing chewable tablet clindamyacin palmitate hydrochloride with easy administration and good taste," Database accession No. 147:102110 (2007). XP002511031.
Zhang, W., "Method for manufacturing chewable tablet clindamyacin palmitate hydrochloride with easy administration and good taste," Database WPI Week 200781, Thomson Scientific, London, GB; AN 2007-874138 (2007). XP002510942.
Form PCT/ISA/220 for corresponding International Application No. PCT/IN2008/000579.
Form PCT/ISA/237 for corresponding International Application No. PCT/IN2008/000579.

* cited by examiner

*Primary Examiner* — Robert A Wax
*Assistant Examiner* — Danah Al-Awadi
(74) *Attorney, Agent, or Firm* — Merchant & Gould P.C.

(57) ABSTRACT

A taste masked pharmaceutical composition of clindamycin, or a pharmaceutically acceptable salt(s), hydrate(s), solvate(s) and physiologically functional derivative(s) and precursors thereof, which includes all polymorphic forms, whether crystalline or amorphous comprising polyhydric alcohol(s); and one or more other pharmaceutically acceptable excipient(s). A process for preparation of a taste masked pharmaceutical composition of clindamycin or a pharmaceutically acceptable salt(s) thereof the said process comprising the steps of a) dry mixing clindamycin, polyhydric alcohol and other pharmaceutically acceptable excipient(s) to get a dry mixture; b) granulating the dry mixture above with a granulating liquid prepared by mixing the suitable pharmaceutically acceptable excipient(s) with aqueous/non-aqueous fluid to obtain a wet mass; c) drying the wet mass to obtain the discrete particles; d) lubricating the discrete particles obtained with a suitable lubricating agent and/or flavor(s).

8 Claims, No Drawings

ORAL COMPOSITIONS OF CLINDAMYCIN

This application is a National Stage Application of PCT/IN2008/000579, filed 10 Sep. 2008, which claims benefit of Serial No. 1242/KOL/2008, filed 22 Jul. 2008 in India and which applications are incorporated herein by reference. To the extent appropriate, a claim of priority is made to each of the above disclosed applications.

FIELD OF THE INVENTION

The present invention pertains to a taste masked and stabilized pharmaceutical composition comprising clindamycin or a pharmaceutically acceptable salt(s), hydrate(s), solvate(s) and physiologically functional derivative(s) and precursor(s) thereof; which includes all polymorphic forms, whether crystalline or amorphous, said composition comprising polyhydric alcohol(s) and the process for preparing it.

BACKGROUND OF INVENTION

The antibiotic Clindamycin (Methyl 7-chloro-6,7,8-trideoxy-6-(1-methyl-trans-4-propyl-L-2-pyrrolidinecarboxamido)-1-thio-L-threo-α-D-galacto-octopyranoside) and its pharmaceutically acceptable salts were originally disclosed and claimed in U.S. Pat. No. 3,580,904 (U.S. Pat. No. '904). The U.S. Pat. No. '904 patent also exemplify a pharmaceutical antibacterial syrup preparation and a method of using it to treat antibacterial diseases. The U.S. Pat. No. 3,655,885 discloses the pediatric syrup formulations for treating lincomycin susceptible bacterial infections.

Clindamycin is a lincosamide antibiotic. It is a semisynthetic antibiotic produced by a 7(S)-chloro substitution of the 7(R)-hydroxyl group of the parent compound lincomycin. Clindamycin is used primarily to treat infections caused by susceptible anaerobic bacteria, including infections of the respiratory tract, septicemia and peritonitis. Clindamycin is also used to treat aerobic bacterial infections and also used to treat some protozoal diseases, such as malaria.

Oral administration constitutes a preferred route for administering Clindamycin. This route is convenient and acceptable to the patients. Conventional dosage forms like tablet, pill, and capsule constitute the solid dosage forms for oral administration. Unfortunately, such formulations may be associated with certain disadvantages such as administering drug formulations to pediatric and geriatric patients, who either may dislike such compositions or may have problem in swallowing. In such situations, oral liquid dosage forms are the preferred choice. However, these dosage forms usually lead to perceptible exposure of the active drug ingredient to the taste buds, which is a very serious problem when the drug has an extremely unpleasant or bitter taste.

The unpleasant taste of the drugs, which are orally administered, is disadvantageous in several aspects. Taste is an important parameter governing the compliance. The disagreeable and unpleasant taste of drugs causes difficulties in swallowing or causes patients to avoid their medication, thereby resulting in low patient compliance. Thus taste-masking technologies are considered important and are developed by many researchers.

U.S. Pat. No. 6,806,256, describes a taste masked oral solution for quinolone-carboxylic acid antibiotic containing sucralose, sugar sweetener and at least one flavoring agent.

US 20080008765 describes taste-masked composition for oral administration of ready to use suspension containing coated particles in a suspension base.

U.S. Pat. No. 5,730,997 describe an oral liquid formulation for antitussives, antihistamines, decongestants, expectorants and mixtures thereof using a high osmolarity system.

Clindamycin like many drug substances has an inherently unpleasant taste (taste and after taste) and odour. This constitutes a significant disadvantage with the existing oral liquid compositions. It is a well-known fact that patients' compliance is low when oral preparations are presented with unpleasant taste and odour.

Artificial flavorings and sweeteners have often been used to mask the taste by generally overwhelming the taste of the pharmaceutical. However, these are often inadequate and the bitter taste remains as a lingering after taste. Other methods of masking the taste include coating the drug with a polymeric material such as ethyl cellulose or an oil, lipid or wax such as paraffins, waxes, beeswax, higher fatty acids, higher fatty acid esters, glycerin fatty acid esters or lecithin, so as to create a barrier and delay the dissolution of the drug. These methods however suffer from the disadvantage of process and formulation complexity and though sometimes suitable for solid dosage forms, in liquid formulations the drug is usually solubilized sufficiently to impart an unpleasant taste. For many drugs, there is an unpleasant taste when dissolved in water-based formulations. Oil-based vehicles are generally not satisfactory for the reason of poor mouth feel and risk of altered bioavailability.

Numerous liquid pharmaceutical compositions for oral administration of clindamycin have been proposed, however there still exists a need for stabilized clindamycin composition with improved taste, and odour for oral administration with good patient compliance and acceptance, especially for children.

Clindamycin is available in the form of oral solution under the brand name of CLEOCIN PEDIATRIC® (Clindamycin) for pediatric patients in the dose of 75 mg/5 ml.

We have now surprisingly found that the unpleasant taste and odour of clindamycin could be substantially improved by the addition of an effective amount polyhydric alcohol in the composition while still maintaining the stability of the composition.

Further the invention provides simple and cost effective manufacturing methods for producing clindamycin composition(s) with good stability and organoleptic properties, and reduction in the total solid content of the composition compared to the marketed formulation.

Thus the invention provides composition(s) of clindamycin with an improved taste; substantially reduced unpleasant odour, and a pleasant mouth feel with substantially unchanged bioavailability using cost effective manufacturing methods.

OBJECT OF THE INVENTION

A taste masked pharmaceutical composition of clindamycin, or a pharmaceutically acceptable salt(s), hydrate(s), solvate(s) and physiologically functional derivative(s) and precursors thereof which includes all polymorphic forms, whether crystalline or amorphous comprising polyhydric alcohol(s); and one or more other pharmaceutically acceptable excipient(s).

Another object of the present invention is to provide a taste masked pharmaceutical composition of clindamycin, wherein the amount of active (free base) is more than about 8% by weight of total solid content of the composition.

Another object of the present invention is a process for preparation of a taste masked pharmaceutical composition of clindamycin or a pharmaceutically acceptable salt(s) thereof the said process comprising the steps of a) dry mixing clindamycin, polyhydric alcohol and other pharmaceutically acceptable excipient(s) to get a dry mixture; b) granulating the dry mixture above with a granulating liquid prepared by mixing the suitable pharmaceutically acceptable excipient(s) with aqueous/non-aqueous fluid to obtain a wet mass; c) drying the wet mass to obtain the discrete particles; d) lubricating the discrete particles obtained with a suitable lubricating agent and/or flavour(s).

Another object of the present invention is a process for preparation of a taste masked pharmaceutical composition of clindamycin or a pharmaceutically acceptable salt(s) thereof the said process comprising the steps of a) melting polyhydric alcohol and mixing with clindamycin and one or more other pharmaceutically acceptable excipient(s) properly to obtain a uniform mass; b) further processing the obtained uniform mass to obtain discrete particles; c) lubricating the discrete particles obtained with a suitable lubricating agent and/or flavour(s).

DETAILED DESCRIPTION OF THE INVENTION

The present invention pertains to a taste-masked pharmaceutical composition of clindamycin, or a pharmaceutically acceptable salt(s) thereof, said composition comprising polyhydric alcohol and one or more other pharmaceutically acceptable excipient(s).

The pharmaceutical composition of the present invention preferably contains polyhydric alcohol(s), flavoring agent(s) sweetening agent(s), and combinations thereof to improve the inherently unpleasant taste and odour associated with clindamycin, and thereby improving the palatability of the present invention.

The term "clindamycin" as used is the invention is meant to cover clindamycin in the form of freebase or its pharmaceutically acceptable salt(s), hydrate(s), solvate(s) and physiologically functional derivative(s) and precursors thereof. The term also includes all polymorphic forms, whether crystalline or amorphous.

Clindamycin may be used as a single active agent, or may be combined with other active agents, vitamins, minerals, dietary supplements, etc. As used herein, "pharmaceutically acceptable salts" refer to derivatives of the clindamycin wherein clindamycin is modified by reacting it with an acid or base as needed to form an ionically bound pair. Examples of pharmaceutically acceptable salts include conventional non-toxic salts or the quaternary ammonium salt of the parent compound formed, for example, from non-toxic inorganic or organic acids. Suitable non-toxic salts include those derived from inorganic acids such as hydrochloric, hydrobromic, sulfuric, sulfamic, phosphoric, nitric, and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, benzoic, salicylic, sulfanilic, fumaric, oxalic, isethionic, and others known to those of ordinarily skilled in the art. The pharmaceutically acceptable salts of the present invention can be synthesized from the clindamycin, by conventional methods. The most preferred salt of clindamycin for the present invention is palmitate hydrochloride salt The term 'taste masking' as used in the invention is meant to refer as perceived reduction of unpleasant taste and/or odour associated with clindamycin in the pharmaceutical composition and/or after stability.

The term 'pharmaceutical composition' as used in the invention is meant to taste and/or odour masked discrete particles comprising clindamycin and one or more pharmaceutically acceptable excipient(s) wherein the composition is solution, suspension, emulsion, microsuspensions, dispersible tablets for solution/suspension or any other liquid or solid composition of clindamycin which can be reconstituted to obtain the liquid dosage form. Preferably the composition of the invention is prepared by dissolving or suspending discrete particles mixture in the liquid excipient base prior to use for oral administration. Preferably the liquid excipient base is water.

The phrase 'pharmaceutically acceptable' as used in the invention is meant to refer to those compounds, materials compositions, or other dosage forms that are, within the scope of medical judgment, suitable for use in contact with tissues of human beings and animals and without excessive toxicity, irritation, allergic response, or any other problem or complication.

The term 'discrete particles' includes within its scope but is not limited to compositions selected from the group comprising powder, granules, microgranules, spheroids, pellets, micropellets, beads, beadlets, microspheres, nanoparticles, microparticles and microcapsules, and dispersible tablets. The discrete particles can be coated or uncoated and can be used preferably in the form of suspension/solution. The discrete particles can be in the form of a unit dose packet (sometimes referred to in the art as a "sachet") in the form of a suspension/solution made from a unit dose packet, in the form of a dose-sipping device or combination thereof e.g. coated pellets filled in a dose sipping device or in a sachet. The use of the term "suspension" herein is intended to embrace liquids containing clindamycin partially in suspension and partially in solution or totally in suspension, and the term 'solution' herein is intended to include compositions comprising clindamycin totally dissolved in the liquid base.

The various techniques can be used for taste masking of clindamycin in the present composition. Various techniques found to be but not limited to use of flavor enhancers, applying polymers on the active ingredients by means of technologies like microencapsulation, complexation with ion exchange resins and inclusion complex formation with cyclodextrins. Other techniques include solubility-limiting methods, incorporation of drugs in vesicles and liposome, and chemical modification. However we have surprisingly found that unpleasant taste and odour of clindamycin can be phenomenally improved by using polyhydric alcohol(s) while maintaining the stability of the dosage form.

The polyhydric alcohol(s) component of the taste-masked composition according to the present invention may be selected from one or more of the group comprising propylene glycol, glycerol, polymers of ethylene glycol, propylene glycol, glycerol such as diethylene glycol, dipropylene glycol and diglycerol, any polymer of ethylene oxide with a molecular weight from 200 to 20,000, etc, and block copolymers of ethylene oxide and propylene oxide commercially known as Poloxamers The poloxamers are commercially available as Pluronic (BASF) and Teric (ICI).The most preferable polyhydric alcohol used in the invention is Polyethylene glycol.

Polyethylene glycols are stable, hydrophilic substances. Polyethylene glycols (PEGs) are widely used in a variety of pharmaceutical formulations including parenteral, topical, ophthalmic, oral, and rectal preparations. Polyethylene glycol is an addition polymer of ethylene oxide and water. Polyethylene glycols are chemically stable in air and in solution. Polyethylene glycols do not support microbial growth, and they do not become rancid. Suitable polyethylene glycols include PEG or its pharmaceutically acceptable derivatives e.g. PEG 200; PEG 300; PEG-400; PEG 540; PEG 600; PEG 900; PEG 1000; PEG 1450; PEG 1500; PEG 1540; PEG 2000; PEG 3000; PEG-3350; PEG 4000; PEG 6000; PEG 8000; PEG 20000; Polyethylene oxide, Pegylated-phospholipids and all the possible pharmaceutically acceptable grades of polyethylene glycol in the art. When used as taste masking agent, polyethylene glycols of higher molecular weight are used in lower concentrations and polyethylene glycols of lower molecular weight are used in higher concentrations. Generally, polyethylene glycol used in the invention is in the range of about 0.5 to about 60% w/v.

The taste-masked pharmaceutical composition of Clindamycin, or a pharmaceutically acceptable salt(s) according to present invention further comprises at least one or more other pharmaceutically acceptable excipient(s) selected from group comprising but not limited to flavouring agent(s), sweetening agents(s), buffering agents(s), preservative(s), viscosity enhancing agents(s), antioxidant(s), wetting agent(s), dispersing agent(s), pH stabilizing agent(s), taste enhancing agent(s), antifoaming agent(s). An excipient can serve multiple functions, for example as both filler and sweetener.

Flavoring agent(s) are used in the invention is meant to impart a pleasant flavor and/or odor to a pharmaceutical composition. Suitable flavoring agents include but not limited to natural and artificial flavors, such as synthetic flavor oils and flavoring aromatics and/or natural oils, extracts from plants, leaves, flowers, fruits and so forth and combinations thereof. Representative suitable flavoring agents may be for example, without limitation, menthol, cinnamon, wintergreen, clove, bay, anise, eucalyptus, thyme, cedar leave, nutmeg, sage, bitter almonds and cassia, vanilla, artificial vanilla, chocolate, artificial chocolate, bubble gum, both natural and artificial fruit flavors, such as cherry flavor, grape flavor, orange flavor, banana flavor, strawberry flavor, lemon flavor, grapefruit flavor and "mint" flavors such as peppermint flavor and spearmint flavor, lime flavor, apple flavor, pear flavor, peach flavor, raspberry flavor, plum flavor, pineapple flavor, apricot flavor and so forth, including combinations of two or more thereof. Flavoring agents are generally provided as a minor component of the composition in amounts effective to provide a palatable flavor to the composition. The amount of flavoring agent may depend on a number of factors, including the desired organoleptic effect. The precise amount of sweetening and/or flavoring agent(s) depends on the properties of the agent(s) used, however generally in an amount that is sufficient to mask the unpleasant taste and/or odor associated with clindamycin as determinable by one skilled in the art. However, flavoring agents generally present is in a pharmaceutically acceptable range.

Sweeteners suitable for inclusion in the present invention may be determined by one skilled in the art including, for example without limitation, both natural and artificial sweeteners such as the representative sweetening agents of intense sweeteners such as sorbitol, sucrose, saccharins such as sodium saccharin, cyclamates such as sodium cyclamates, aspartame, sucralose, thaumatin, acesulfam K, and the like, and sugars such as monosaccharides, disaccharides and polysaccharides. Representative sugars useful in the present invention include, without limitation, xylose, ribose, glucose, mannose, galactose, fructose, dextrose, sucrose, maltose, partially hydrolyzed starch or corn syrup, and sugar alcohols such as sorbitol, xylitol, mannitol, glycerin, etc. and combination thereof. Presently preferred as a sugar sweetener is sucralose. Sugar sweeteners may be replaced or augmented by water-soluble artificial sweeteners, such as the suitable artificial sweeteners previously listed and mixtures thereof. The amount of artificial sweetener used in the composition may vary to provide an appropriate amount of sweetness as determinable by one skilled in the art. Mixtures of sweetening and/or flavoring agents are preferably used.

Examples of preservatives suitable for use in the present invention include, for example without limitation, one or more alkyl hydroxybenzoates, such as methyl hydroxybenzoates, ethyl hydroxybenzoates, propyl hydroxybenzoates, butyl hydroxybenzoates and the like. Additional preservatives useful in the present invention include, but are not limited to, sodium benzoate, potassium sorbate, salts of edetate (also know as salts of ethylenediaminetetraacetic acid, or EDTA, such as disodium edetate) and antimicrobial agents including parabens (p-hydroxybenzoic acids esters) such as methyl paraben, ethylparaben, propylparaben, butylparaben and the like, and combinations thereof. Parabens are preferred, with methyl paraben most preferred for use as preservative ingredients to add to the present pharmaceutical composition, although other pharmaceutically acceptable preservatives may be substituted therefore. Preservative(s) as used in the composition are in a pharmaceutically acceptable range.

The pharmaceutical composition may also contain a viscosity enhancing agent(s) which include but are not limited to gums; sorbitol; glycerol; polyvinyl alcohol; polyvinyl pyrrolidone; polyethylene oxide; cellulose derivatives, such as hydroxypropylmethylcellulose or a salt thereof, alkyl ether of cellulose, such as methylcellulose, ethylcellulose, hydroxyethylcellulose, hydroxyethylmethylcellulose and mixtures thereof. Preferably the viscosity-enhancing agent is hydroxypropylmethylcellulose e.g. (HPMC K4M, HPMC K100 LVP; HPMC K15 MP; HPMC E4 MP; HPMC E10 MP CR).

The pharmaceutical composition may also contain a dispersing agent(s), which include but are not limited to, colloidal silicon dioxide and surfactants, wherein the surfactant is used alone or as an admixture with one or more surfactant. Combinations of colloidal silicon dioxide with one or more surfactants can also be used and other pharmaceutically accepted dispersing agents.

The pharmaceutical composition may also contain a pH—stabilizing agent to maintain a desired pH. The term "pH—stabilizing agent" encompasses buffers and pH—altering agents. Suitable pH—stabilizing agents include but not limited to tribasic sodium phosphate, anhydrous sodium carbonate, glycine, citric acid or mixtures thereof.

Preferably the pH of the composition is in range of about 2.5 -about 5.5.

Most preferably the pH of composition is in range from about 2.5 -about 3.0

The pharmaceutical composition may also contain wetting agent(s) which include, but are not limited to such as sorbitan monolaurate, polysorbate 80, and sodium lauryl sulfate and the like.

The pharmaceutical composition may also contain taste enhancing agents which include, but are not limited to, sodium chloride, glycine, maltose, dextrose, maltodextrin, citric acid, tartaric acid and the like and mixtures thereof.

The pharmaceutical composition may also contain suitable coloring agent(s) to provide an appealing color to the pharmaceutical composition, which include, but are not limited to, titanium dioxide pigments, lake colors and iron oxide pigments.

The pharmaceutical suspension composition may also contain suitable antifoaming agents, which include, but are not limited to simethicone emulsion, dimethicone, lutrol and the like.

The pharmaceutical composition may also contain antioxidant(s) which include, but are not limited to such as tocopherols, gallic acid and gallates, butylated hydroxy anisole, butylated hydroxy toluene, ascorbic acid, maleic acid, sodium bisulphate, sodium metabisulphite, sodiumformaldehyde sulphoxylate and the like.

The pharmaceutical composition may also contain suitable lubricants and flow aids such as, but not limited to, talc, magnesium stearate, calcium silicate, 1-leucine and colloidal silicon dioxide.

All these excipients can be used at levels well known to the persons skilled in the art.

The specifically mentioned pharmaceutically acceptable excipient(s) are intended to be exemplary, not exhaustive, of specific excipients that may be used in the practice of the disclosed invention. It is further understood that more than one of any particular type of excipient may be used in the compositions described herein. For example, the compositions may include more than one flavorant, colorant, etc. Also, a single excipient may provide multiple functions.

Further the compositions of the present invention comprises more than about 8% of active (free base) by weight of total solid content of the composition. The present invention comprises preferably more than about 10% of active (free base) by weight of total solid content of the composition.

It has been found that the clindamycin composition of present invention has less solid content compared to the innovator. The marketed clindamycin formulation CLEOCIN PEDIATRIC® (Clindamycin)) has about 40 gm of solid content to be reconstituted before use compared to the invention which has about 13 gm of solid content, thereby reducing the solid content to about thrice comparative to the innovator with improved taste, odor and more stability compared to the innovator. Thus by using present invention the solid content of the composition has substantially reduced compared to the innovator with improvement in the organoleptic properties.

An clindamycin discrete particles for in accordance with the present invention may be supplied in bottles which upon reconstitution, for example, aqueous media will preferable contain 75 mg of clindamycin/5 ml. The discrete particles can also be supplied in unit dosage of packets or sachets that, upon reconstitution in aqueous media, provide a unit dose of clindamycin.

The composition(s) of the present invention can be prepared by means well known to those skilled in the art such as but not limited to dry mixing, dry granulation, direct compression, wet granulation (which can be aqueous or non aqueous solvent(s)).

The solvent(s) used in aqueous or non-aqueous granulation in the present invention include all the solvents well known in the art.

For example, the discrete particles for the present invention can be prepared by a process comprising the steps of a) dry mixing clindamycin, polyhydric alcohol and other pharmaceutically acceptable excipient(s) to get a dry mixture; b) granulating the dry mixture above with a granulating liquid prepared by mixing the suitable pharmaceutically acceptable excipient(s) with aqueous/non-aqueous fluid to obtain a wet mass; c) drying the wet mass to obtain the discrete particles; d) lubricating the discrete particles obtained with a suitable lubricating agent and/or flavour(s).

The discrete particles of the present invention can also be prepared by a process comprising the steps of a) melting polyhydric alcohol and mixing with clindamycin and one or more other pharmaceutically acceptable excipient(s) properly to obtain a uniform mass; b) further processing the obtained uniform mass to obtain discrete particles; c) lubricating the discrete particles obtained with a suitable lubricating agent and/or flavour(s).

Where applicable, the discrete particles for the invention can be reconstituted using potable water or using juices such as apple juice, strawberry juice, orange juice or using aerated or carbonated preparations. Alternatively, for the suspension per se, vehicles well known to persons skilled in the art, such as propylene glycol, glycerin, sucrose solution, sorbitol, liquid glucose and the like can also be used, at levels well known to the persons skilled in the art, in addition to water The following examples are illustrative of the present invention, and the examples should not be considered as limiting the scope of this invention in any way, as these examples and other equivalents thereof will become apparent to those versed in the art, in the light of the present disclosure, and the accompanying claims.

EXAMPLES

Example 1

| Sr. No. | Ingredient | Quantity |
| --- | --- | --- |
| 1. | *Clindamycin Palmitate Hydrochloride | 2.646 gm |
| 2. | Polyethyleneglycol (PEG) | 1-25% |
| 3. | Artificial sweetener | 0.1-0.5% |
| 4. | Dextrin | 2-20% |
| 5. | Sucrose | 5-50% |
| 6. | Preservative | 0.01-0.1% |
| 7. | Flavors | Upto 1% |
| 8. | Wetting agent | 0.1-1.0% |

*(Equivalent to 1.5 gm of Clindamycin freebase)

Procedure:

Step1:

Melt PEG (Temperature NMT 60° C.); add preservative to melted PEG, mix thoroughly to ensure complete mixing. Pass Clindamycin, Dextrin, Artificial sweetener, Sucrose and suitable wetting agent through suitable mesh and mix them geometrically. Add this mixture to melted PEG and stir continuously to ensure complete mixing to get a uniform mass. Cool the blend to room temperature with constant stirring. Pass the solidified blend through suitable sieve and collect the granules.

Step2:

Lubricate the granules of Step1 using suitable flavors and reconstitute it before administration.

Example 2

| Sr. No. | Ingredient | Quantity |
| --- | --- | --- |
| 1 | *Clindamycin Palmitate Hydrochloride | 2.646 gm |
| 2 | Polyethylene glycol (PEG) | 1-30% |
| 3 | Artificial sweetener | 0.1-0.5% |
| 4 | Dextrin | 5-25% |
| 5 | Preservative | 0.01-0.1% |
| 6 | Flavors | Upto 1% |
| 7 | Wetting agent | 0.1-1.0% |
| 8 | Mannitol | 5-25% |

*(Equivalent to 1.5 gm of Clindamycin free base)

Procedure:

Step1:

Melt PEG (Temperature NMT 60° C.); add preservative to melted PEG, mix thoroughly to ensure complete mixing. Pass Clindamycin, Dextrin, Mannitol, Artificial sweetener and suitable wetting agent through suitable mesh and mix them geometrically. Add this mixture to melted PEG and stir continuously to ensure complete mixing to get a uniform mass. Cool the blend to room temperature with constant stirring. Pass the solidified blend through suitable sieve and collect the granules.

Step2:

Lubricate the granules of Step1 using suitable flavors and reconstitute it before administration.

Example 3

| Sr. No. | Ingredient | Quantity |
| --- | --- | --- |
| 1 | *Clindamycin Palmitate Hydrochloride | 2.646 gm |
| 2 | Polyethylene glycol (PEG) | 1-15% |
| 3 | Artificial sweetener | 0.1-0.5% |
| 4 | Dextrin | 5-20% |
| 5 | Sucrose | 5-20% |
| 6 | Preservative | 0.01-0.1% |
| 7 | Flavors | Upto 1% |
| 8 | Wetting agent | 0.1-1.0% |
| 9 | Lactose | 5-15% |

*(Equivalent to 1.5 gm of Clindamycin freebase)

Procedure:

Step1:

Melt PEG (Temperature NMT 60° C.); add preservative to melted PEG followed by addition of Clindamycin, stir continuously to ensure complete mixing to get a uniform mass. Cool the blend to room temperature with constant stirring. Pass the solidified blend through suitable sieve and collect the granules.

Step2: Pass, Dextrin, Sucrose, Lactose, Artificial sweetener and suitable wetting agent through suitable mesh and mix them geometrically.

Step3: Mix the blend of step 2 with granules of step1.

Step4: Lubricate the mix of Step3 using suitable flavors and reconstitute it before administration.

Example 4

| Sr. No. | Ingredient | Quantity |
| --- | --- | --- |
| 1 | *Clindamycin Palmitate Hydrochloride | 2.646 gm |
| 2 | Polyethylene glycol (PEG) | 1-15% |
| 3 | Artificial sweetener | 0.1-0.5% |
| 4 | Dextrin | 2-20% |
| 5 | Sucrose | 5-50% |
| 6 | Preservative | 0.01-0.1% |
| 7 | Flavors | Upto 1% |
| 8 | Wetting agent | 0.1-1.0% |
| 9 | Sucrose solution | Q.s |

*(Equivalent to 1.5 gm of Clindamycin freebase)

Procedure:

Step1:

Procedure-Pass Clindamycin, PEG, Dextrin, Wetting agent, artificial sweetener, Preservative and Sucrose through suitable mesh and mix them geometrically. Granulate this mixture using Sucrose solution. Dry the mass for 15-20 min at 40° C. Pass the dried mass through suitable sieve and collect the granules.

Step2: Lubricate the granules of Step1 using suitable flavors and reconstitute it before administration.

Example 5

| Sr. No. | Ingredient | Quantity |
| --- | --- | --- |
| 1 | *Clindamycin Palmitate Hydrochloride | 2.646 gm |
| 2 | Polyethylene glycol (PEG) | 1-25% |
| 3 | Artificial sweetener | 0.1-0.5% |
| 4 | Dextrin | 2-20% |
| 5 | Sucrose | 5-50% |
| 6 | Preservative | 0.01-0.1% |
| 7 | Flavors | Upto 1% |
| 8 | Wetting agent | 0.1-1.0% |
| 9 | Isopropyl alcohol | Q.s |

*(Equivalent to 1.5 gm of Clindamycin freebase)

Procedure:

Step1: Pass Clindamycin, PEG, Dextrin, Wetting agent, Artificial sweetener, Preservative and Sucrose through suitable mesh and mix them geometrically. Granulate this mixture using isopropyl alcohol as a granulating aid. Dry the mass for 15-20 min at 40° C. Pass the dried mass through suitable sieve and collect the granules Step2: Lubricate the granules of Step1 using suitable flavors and reconstitute it before administration.

Example 6

| Sr. No. | Ingredient | Quantity |
| --- | --- | --- |
| 1 | *Clindamycin Palmitate Hydrochloride | 2.646 gm |
| 2 | Polyethylene glycol (PEG) | 1-20% |
| 3 | Artificial sweetener | 0.1-0.5% |
| 4 | Dextrin | 2-20% |
| 5 | Sucrose | 5-50% |
| 6 | Preservative | 0.01-0.1% |
| 7 | Flavors | Upto 1% |
| 8 | Wetting agent | 0.1-1.0% |
| 9 | Poly vinyl Pyrrolidone | 0.5-1.0% |
| 10 | Isopropyl alcohol | Q.s |

*(Equivalent to 1.5 gm of Clindamycin freebase)

Procedure:

Step1: Pass Clindamycin, PEG, Dextrin, Wetting agent, Artificial sweetener, Preservative and Sucrose through suitable mesh and mix them geometrically. Granulate this mixture using Poly vinyl Pyrrolidone and isopropyl alcohol solution as a granulating aid. Dry the mass for 15-20 min at 40° C. and collect the final granules from suitable sieve.

Step2: Lubricate the granules of Step1 using suitable flavors and reconstitute it before administration.

Example 7

| Sr. No. | Ingredient | Quantity |
| --- | --- | --- |
| 1 | *Clindamycin Palmitate Hydrochloride | 2.646 gm |

| Sr. No. | Ingredient | Quantity |
|---|---|---|
| 2 | Polyethylene glycol | 1-15% |
| 3 | Artificial sweetener | 0.1-0.5% |
| 4 | Dextrin | 2-20% |
| 5 | Preservative | 0.01-0.1% |
| 6 | Flavors | Upto 1% |
| 7 | Wetting agent | 0.1-1.0% |
| 8 | Hypromellose (HPMC) | 0.1-0.5% |
| 9 | Water | Q.s |
| 10 | Lactose | 5-15% |

*(Equivalent to 1.5 gm of Clindamycin freebase)

Procedure:

Step 1: Pass Clindamycin, PEG, Dextrin, Wetting agent, Artificial sweetener, Lactose and Preservative through suitable mesh and mix them geometrically. Granulate this mixture using Hypromellose and water solution as a granulating aid. Dry the mass for 15-20 min at 40° C. Pass the dried mass through suitable sieve and collect the granules Step 2: Lubricate the granules of Step 1 using suitable flavors and reconstitute it before administration Example 8

| Sr. No | Ingredients | |
|---|---|---|
| Step 1-Drug loading on sugar spheres | | |
| | | Qty (gm) |
| 1 | Sugar spheres | 250 |
| 2 | HPMC | 0.1-5% |
| 3 | Clindamycin Palmitate Hydrochloride | 25-50% |
| 4 | Ethyl Alcohol | Q.s |
| Step 2-Eudragit coating | | |
| | | Qty (gm) |
| 1 | Clindamycin Palmitate Hydrochloride loaded spheres | 250 |
| 2 | Eudragit | 5-25% |
| 3 | Iso Propyl alcohol | Q.s |
| 4 | Acetone | Q.s |
| 5 | Water | Q.s |
| Step 3-Preparation of suspension base | | |
| | | Quantity/bottle |
| 1 | Artificial sweetener | 0.1-0.5% |
| 2 | Viscosity enhancing agent | 0.05-4% |
| 3 | Polyethylene glycol (PEG) | 1-15% |
| 4 | Opacifier | 0.1-2% |
| 5 | Preservative | 0.01-0.1% |
| 6 | Flavors | Up to 1% |
| 7 | Lubricant | 0.05-1.5% |

Procedure: Step 1 and Step 2 were performed using Fluid Bed coater. All the ingredients of step 3 were passed through suitable sieve and mixed thoroughly with the Eudragit coated drug loaded pellets. Dry suspension powder thus formed was then filled in final containers, which is reconstituted before administration.

Example 9

| Sr. No. | Ingredient | Quantity |
|---|---|---|
| 1 | *Clindamycin Palmitate Hydrochloride | 2.646 gm |
| 2 | Polyethylene glycol (PEG) | 1-25% |
| 3 | Artificial sweetener | 0.1-0.5% |
| 4 | Dextrin | 2-20% |
| 5 | Sucrose | 5-50% |
| 6 | Preservative | 0.01-0.1% |
| 7 | Flavors | Up to 1% |
| 8 | Wetting agent | 0.1-1.0% |

Procedure—Pass Clindamycin, PEG, Dextrin, Wetting agent, Artificial sweetener, Preservative, Sucrose and flavors through suitable mesh and mix them geometrically to assure complete mixing. Dry powder thus formed was then filled in final containers, which is reconstituted before administration.

Evaluation of Taste Masking Effect: Sensory Test 20 healthy volunteers involved in the study were exposed to the taste of the reconstituted Innovator's Formulation (CLEOCIN PEDIATRIC® (Clindamycin)) and Example 1, 4 and 5 of present invention on day 1, day 7 and day 14. The liquid compositions were subjected to sensory test. Each of the liquid composition was actually put in the mouth of twenty volunteers, in an amount equivalent to 75 mg of the liquid clindamycin palmitate hydrochloride. The results indicated that Example 1 and 5 has better acceptance than the marketed CLEOCIN PEDIATRIC® (Clindamycin).

Evaluation of Odor Test 20 healthy volunteers involved in the study were exposed to the smell of the reconstituted Innovator's Formulation (CLEOCIN PEDIATRIC® (Clindamycin)) and Example 1, 4 and 5 of present invention on day 1, day 7 and day 14. Their like/dislike for the odor of the compositions was ranked as preferred/ not preferred followed by the qualitative interpretation of their response. The recorded responses are as mentioned below in Table No. 1:

TABLE NO. 1

Comparative Evaluation of Odor test

| DURATION (DAYS) | Example 1 (% PREFERRED) | Example 4 (% PREFERRED) | Example 5 (% PREFERRED) | INNOVATOR (% PREFERRED) |
|---|---|---|---|---|
| DAY 1 | 80 | 70 | 80 | 20 |
| DAY 7 | 90 | 80 | 70 | 10 |
| DAY 14 | 90 | 80 | 90 | 10 |

The results indicate that Example 1 and 5 are preferred comparatively to the marketed formulation.

Stability Data:

Accelerated Stability Studies as per ICH guidelines, have been performed for the compositions at room temperature (RT), at 40° C. and at 60° C. As per the observations made the composition of the present invention are more stable than Innovator's Formulation (CLEOCIN PEDIATRIC® (Clindamycin)) under the conditions mentioned.

The invention claimed is:

1. A taste masked pharmaceutical liquid composition, comprising:
   clindamycin palmitate hydrochloride in an amount 2.646 g; polyethylene glycol; dextrin; sucrose; and optionally artificial sweetener, preservative, flavoring or wetting agent;
   wherein clindamycin palmitate hydrochloride is equivalent to 1.5 g of clindamycin free base.

2. The taste-masked composition according to claim 1 wherein the artificial sweetener is selected from the group consisting of sorbitol, sucrose, saccharin, cyclamates, aspartame, sucralose, thaumatin, acesulfam K, and sugar.

3. The composition of claim 2, wherein the sugar comprises monosaccharide, disaccharide, or polysaccharide.

4. The taste-masked composition according to claim 1, wherein the preservative is selected from the group consisting of alkyl hydroxybenzoate, sodium benzoate, potassium sorbate, salts of edetate, and antimicrobial agent.

5. The composition of claim 4, wherein the antimicrobial agent comprises a paraben.

6. The taste-masked composition according to claim 1, wherein the flavouring agent is selected from the group consisting of menthol, cinnamon, wintergreen, clove, bay, anise, eucalyptus, thyme, cedar leave, nutmeg, sage, bitter almond, cassia, natural vanilla, artificial vanilla, natural chocolate, artificial chocolate, bubble gum, natural fruit flavor, and artificial fruit flavor.

7. The taste-masked composition according to claim 1, wherein the wetting agent is selected from the group consisting of sorbitan monolaurate, polysorbate 80, and sodium lauryl sulfate.

8. The taste-masked composition according to claim 1, comprising about 1% to about 30% of polyethylene glycol.

* * * * *